(12) United States Patent
Shioda et al.

(10) Patent No.: US 9,104,912 B2
(45) Date of Patent: Aug. 11, 2015

(54) APPARATUS AND METHOD FOR MEASURING ELECTROMAGNETIC WAVE

(75) Inventors: Michinori Shioda, Yokohama (JP); Toshihiko Ouchi, Machida (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 76 days.

(21) Appl. No.: 13/520,701

(22) PCT Filed: Dec. 28, 2010

(86) PCT No.: PCT/JP2010/007591
§ 371 (c)(1),
(2), (4) Date: Jul. 5, 2012

(87) PCT Pub. No.: WO2011/083558
PCT Pub. Date: Jul. 14, 2011

(65) Prior Publication Data
US 2012/0280128 A1    Nov. 8, 2012

(30) Foreign Application Priority Data
Jan. 8, 2010   (JP) ................................ 2010-002481

(51) Int. Cl.
  *G01J 5/00*    (2006.01)
  *G06K 9/00*    (2006.01)
  *G01N 21/3581* (2014.01)

(52) U.S. Cl.
  CPC ........ *G06K 9/00516* (2013.01); *G01N 21/3581* (2013.01)

(58) Field of Classification Search
  USPC ............................................. 250/338.1, 340
  See application file for complete search history.

(56) References Cited

U.S. PATENT DOCUMENTS 5,784,285 A * 7/1998 Tamaki et al. .................. 702/66
5,939,721 A   8/1999 Jacobsen et al.
(Continued)

FOREIGN PATENT DOCUMENTS

| CN | 101377406 A | 3/2009 |
| EP | 2196791 A2 | 6/2010 |
| JP | 10-153547 A | 6/1998 |
| JP | 2004-101510 A | 4/2004 |
| WO | 2009/084712 A1 | 7/2009 |

OTHER PUBLICATIONS

Author: JWHandley, A J Fitzgerald, E Berry and R D Boyle1 , Title: Wavelet compression in medical terahertz pulsed imaging, Date: Oct. 17, 2002, Publisher: Institute of Physics Publishing, Physics in Medicine and Biology, Edition: Phys. Med. Biol. 47 (2002) 3885-3892.*
Bradley Ferguson et al., "De-Noising Techniques for Terahertz Responses of Biological Samples," Microelectronics Journal, vol. 32 (2001), No. 12, Dec. 1, 2001, pp. 943-953.

(Continued)

*Primary Examiner* — David J Makiya
*Assistant Examiner* — Taeho Jo
(74) *Attorney, Agent, or Firm* — Canon USA, Inc. IP Division

(57) ABSTRACT

The present invention provides an apparatus and a method for transforming a time waveform of an electromagnetic wave into a time waveform suited for signal processing and the like so as to measure the time waveform.
A wavelet transform is performed on a first time waveform of an electromagnetic wave, such as a terahertz wave, measured in advance, and a second time waveform suited for signal processing and having a high correlation with a mother wavelet used in the wavelet transform is formed by controlling a wavelet expansion coefficient. In a second measurement process and onward of a target object, a transforming unit, such as a bias voltage controller, is used to transform the electromagnetic wave into a transformed time waveform so as to measure the time waveform.

11 Claims, 6 Drawing Sheets

(56) References Cited

U.S. PATENT DOCUMENTS

| | | | |
|---|---|---|---|
| 7,738,111 B2* | 6/2010 | Bennett | 356/484 |
| 7,746,400 B2* | 6/2010 | Mo | 348/308 |
| 8,527,227 B2* | 9/2013 | Shioda | 702/77 |
| 2008/0315098 A1* | 12/2008 | Itsuji | 250/330 |
| 2009/0302223 A1* | 12/2009 | Tamada et al. | 250/340 |
| 2010/0148071 A1* | 6/2010 | Shioda | 250/341.8 |
| 2010/0258727 A1* | 10/2010 | Itsuji et al. | 250/338.4 |
| 2011/0068268 A1* | 3/2011 | Heidari | 250/330 |
| 2011/0184654 A1* | 7/2011 | Ben-David et al. | 702/19 |

OTHER PUBLICATIONS

Roberto K. H. Galvao et al., "Optimal Discrimination and Classification of THz Spectra in the Wavelet Domain," Optic Express, vol. 11, No. 12, Jun. 6, 2003, pp. 1462-1473.

D.M. Mittleman et al., "Gas Sensing Using Terahertz Time-Domain Spectroscopy," Applied Physics B, Laser and Optics, vol. B67, No. 3, Sep. 1, 1998, pp. 379-390.

Yang Chen et al., "Stationary-Wavelet Regularized Inverse Filtering: A Robust Deconvolution Approach for Terahertz Reflection Imaging," IEEE 2009, Sep. 21, 2009, pp. 1-2.

Richard S. Ardolino, "Wavelet-Based Signal Processing of Electromagnetic Pulse Generated Waveforms," Naval Postgraduate School, Sep. 2007, pp. 1-104.

James W. Handley, "Time Frequency Analysis Techniques in Terahertz Pulsed Imaging," The University of Leeds, School of Computing, Dec. 2003, pp. 1-166.

Carl Taswell; "The What, How, and Why of Wavelet Shrinkage Denoising;" Computing in Science and Engineering; May/Jun. 2000; pp. 12-19.

* cited by examiner

APPARATUS AND METHOD FOR MEASURING ELECTROMAGNETIC WAVE

TECHNICAL FIELD

The present invention relates to technologies for measuring information such as waveforms of electromagnetic waves. In particular, the present invention relates to an apparatus and a method for measuring a terahertz wave as a waveform suited for signal processing.

BACKGROUND ART

In recent years, non-destructive transillumination imaging using terahertz waves and terahertz time-domain spectroscopy for studying the characteristics of materials using terahertz wave pulses have been actively studied. PTL discloses a method that relates to image processing performed in terahertz imaging and that uses wavelet analysis for information compression and peak detection. Furthermore, NPL discloses performing a wavelet transform on a time waveform of a terahertz wave and setting a value of a wavelet expansion coefficient that is smaller than a threshold value to zero (threshold processing). Accordingly, a noise component included in the time waveform can be removed. By performing an inverse wavelet transform after removing the noise component, a time waveform with the noise component removed therefrom can be obtained. NPL discusses comparing S/N ratios after the removal of the noise component so as to determine which mother wavelet has the greatest amount of noise component removed therefrom among various mother wavelets. The noise component mainly expresses white noise occurring over the entire frequency range. Due to having a low correlation with a mother wavelet, the noise component occurs near zero with respect to each expansion coefficient.

CITATION LIST

Patent Literature

PTL 1: Japanese Patent Laid-Open No. 10-153547

Non Patent Literature

NPL 1: Microelectronics Journal, Vol. 32 (2001), pp. 943-953, "De-noising techniques for terahertz responses of biological samples"

SUMMARY OF INVENTION

Technical Problem

In the aforementioned de-noising technique, a signal (i.e., expansion coefficient value) deriving from the time waveform to be determined also includes a component having a low correlation with a mother wavelet. This means that a signal in which a wavelet expansion coefficient value is close to zero also includes such a signal deriving from the time waveform in addition to the noise component. Therefore, the de-noising method based on the wavelet transform in the related art described above undesirably removes this signal deriving from the time waveform.

Solution to Problem

In view of the aforementioned problems, an electromagnetic-wave measuring apparatus of the present invention for measuring an electromagnetic wave includes a waveform obtaining unit, a forming unit, and a transforming unit. The waveform obtaining unit is configured to obtain a first time waveform of the electromagnetic wave. The forming unit is configured to perform a wavelet transform on the first time waveform and to perform an inverse wavelet transform by using a controlled wavelet expansion coefficient so as to form a second time waveform. The transforming unit is configured to obtain a transformed time waveform by transforming the electromagnetic wave into the transformed time waveform on the basis of a ratio between the first time waveform and the second time waveform.

Furthermore, in view of the aforementioned problems, an electromagnetic-wave measuring method of the present invention for measuring an electromagnetic wave includes the following steps: a first step for obtaining a first time waveform of the electromagnetic wave; a second step for performing a wavelet transform on the first time waveform; a third step for performing an inverse wavelet transform on a result of the wavelet transform by using a controlled wavelet expansion coefficient so as to obtain a second time waveform; a fourth step for determining a ratio between the first time waveform and the second time waveform; and a fifth step for obtaining a transformed time waveform by transforming the electromagnetic wave into the transformed time waveform on the basis of the ratio.

Advantageous Effects of Invention

According to the present invention, since a time waveform is obtained by transforming the electromagnetic wave into the second time waveform on the basis of the aforementioned ratio, the undesired removal of a signal deriving from the time waveform to be determined, which occurred when removing a noise component included in the time waveform by using threshold processing or the like in the related art, can be prevented.

DESCRIPTION OF EMBODIMENTS

Figure 1A:
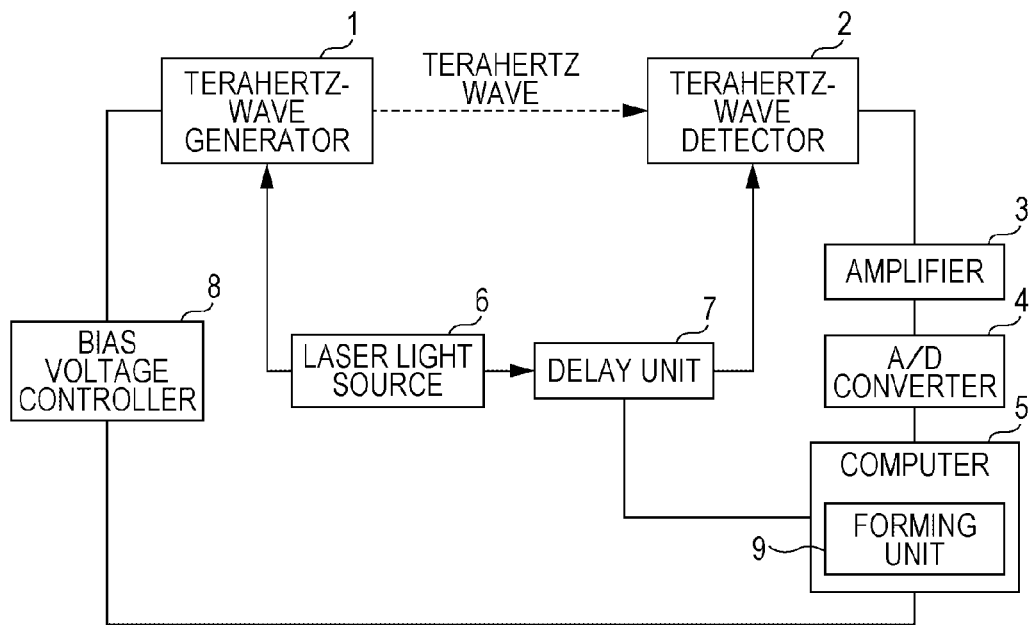
FIG. 1A is a configuration diagram of an embodiment of the present invention.

An embodiment according to the present invention will be described below. First, a first time waveform of an electromagnetic wave, such as a terahertz wave (i.e., an electromagnetic wave including a component with a frequency ranging between 30 GHz and 30 THz) is obtained and undergoes a wavelet transform. Then, a second time waveform is obtained by performing an inverse wavelet transform on this result by using wavelet expansion coefficients controlled by threshold processing or the like. Subsequently, when obtaining a time waveform of a subsequent electromagnetic wave, the time waveform is obtained by transforming the electromagnetic wave into a second time waveform on the basis of a ratio between the first time waveform and the second time waveform. Specifically, the first time waveform is obtained, for example, by using a detector that detects the electromagnetic wave, a generator that generates the electromagnetic wave, and a delay unit that adjusts a delay time between a point at which the electromagnetic wave is generated and a point at which the electromagnetic wave is detected, and by varying the delay time using the delay unit. The second time waveform can be made a waveform suited for signal processing and having a high correlation with a mother wavelet used in the aforementioned wavelet transform. When actually measuring the time waveform of the electromagnetic wave, the second time waveform is measured, for example, while varying the value of data obtained for each delay time on the basis of the aforementioned ratio. Examples of methods of varying the value of data include a method of varying a bias voltage to be applied to the generator by using a controller, a method of varying the light irradiation power of laser to be irradiated onto the generator by using a variable attenuator, and a method of varying the amplification factor of a variable amplifier that amplifies a signal from the detector. Another method involves using an arithmetic device provided for a computer.

Furthermore, the time waveform of the electromagnetic wave can also be formed by performing a wavelet transform on the second time waveform obtained on the basis of the aforementioned ratio and then performing an inverse wavelet transform by controlling the wavelet expansion coefficients. In this case, the second time waveform is a time waveform that does not include a component having a low correlation with the mother wavelet. Therefore, even when the threshold processing in the related art were to be applied, a noise component included in the time waveform to be determined can be removed without removing a signal deriving from the time waveform. Specifically, this second time waveform is a time waveform in which the wavelet expansion coefficients having a low correlation with the mother wavelet are set to zero so as to facilitate the processing. Hence, if the values of these wavelet expansion coefficients are small but not zero, the wavelet expansion coefficients are considered as being noise, and the wavelet expansion coefficients are set to zero again so that the noise component alone can be removed. In this manner, in a second measurement process and onward, a second time waveform is generated (that is, transformed) using the aforementioned ratio, but this second time waveform is a waveform that has already undergone control, such as threshold processing. Accordingly, in the second measurement process and onward, highly accurate measurement can be performed at high speed.

The measurement technique according to the present invention can be used for, for example, examining a target measurement object (e.g., identifying a target object such as a medicinal drug). First, in a first measurement process, a time waveform (first time waveform) of an electromagnetic wave, such as a terahertz wave, is obtained by using a reference object. In this case, a time waveform with a high S/N ratio is obtained by taking a sufficient amount of time by performing commonly used processing, such as averaging. Then, a time waveform (second time waveform) that does not include a component having a low correlation with the mother wavelet is obtained by performing control, such as threshold processing, by using wavelet transform. The component removed by performing control such as threshold processing at this stage can possibly include a component deriving from the time waveform (i.e., a component deriving from the time waveform but having a low correlation with the mother wavelet) in addition to a noise component (mainly white noise). Subsequently, a ratio between the first time waveform and the second time waveform is determined. Moreover, in a second measurement process and onward of the target object, a transformed time waveform is generated (transformed) using this ratio (by, for example, controlling a bias voltage to be applied to a photoconductor at the generator side) so as to obtain a time waveform of the target object resembling the reference object at high speed. Furthermore, by performing threshold processing, noise can be removed from the time waveform obtained at high speed. The component removed by performing threshold processing at this stage does not include the component deriving from the time waveform.

The second time waveform is normally generated (transformed) in the following manner. For each delay time, the ratio between the value of the first time waveform and the value of the second time waveform is determined. The determined ratio is multiplied by the first time waveform so that a dummy waveform with no wavelet expansion coefficients that correspond to a noise level can be formed. Specifically, the first time waveform corresponds to the normally-measured original electromagnetic wave, such as the terahertz wave. On the other hand, when the transformed time waveform is measured, the measured transformed time waveform is a transformed time waveform measured by, for example, temporally varying the voltage and thus differs from a transformed time waveform obtained by measuring an actual electromagnetic wave travelling through space. In other words, the transformed time waveform is a dummy transformed time waveform formed by devising the measurement method so as to facilitate the subsequent processing. By transforming the first time waveform of the terahertz wave or the like measured in the related art into the transformed time waveform having no wavelet expansion coefficients that correspond to the noise level in this manner, the S/N ratio can be improved relative to that in the related art. Furthermore, when examining the target object, the time waveform that does not include the component having a low correlation with the mother wavelet is obtained in the first measurement process so that the target object resembling the reference object can be sequentially examined at high speed in the second measurement process and onward.

Furthermore, based on the above concept, an electromagnetic-wave measuring apparatus according to the present invention can be formed by including a waveform obtaining unit that obtains the first time waveform of the electromagnetic wave, a forming unit, and a transforming unit. As mentioned above, the forming unit forms the second time waveform by performing the wavelet transform on the first time waveform and then performing the inverse wavelet transform using the wavelet expansion coefficients controlled by threshold processing or the like. As mentioned above, when the time waveform of the electromagnetic wave is to be obtained, the transforming unit obtains the transformed time waveform by transforming the electromagnetic wave into the transformed time waveform on the basis of the ratio between the first time waveform and the second time waveform. In the case where a terahertz wave is used, the waveform obtaining unit includes, for example, a terahertz-wave generator, a terahertz-wave detector, and a delay unit that adjusts the delay time between a point at which the terahertz wave is generated and a point at which the terahertz wave is detected. The terahertz wave is measured by varying the delay time.

The forming unit forms the second time waveform that is suited for signal processing and that has a high correlation with the mother wavelet used in the wavelet transform. Examples of methods for controlling the wavelet expansion coefficients include a method of replacing the wavelet expansion coefficients other than those having large absolute values with zero and a method of replacing the wavelet expansion coefficients having a small effect on the shape of the time waveform with zero. An important point is that the time waveform be formed by reducing the number of wavelet expansion coefficients as much as possible. Because a time waveform expressed by a minimum number of wavelet expansion coefficients has a small area with a mixture of signal and noise, the time waveform is suited for signal processing.

Examples of mother wavelets to be used in the aforementioned apparatus and the aforementioned method include Coiflet 4 and Symlet 10 having shapes that relatively resemble the shape of an electromagnetic wave, such as a terahertz waveform.

Next, specific embodiments of the apparatus and the method for transforming a waveform of an electromagnetic wave to be measured into a waveform suited for signal processing will be described. In order to simplify the description in the following embodiments, an apparatus and a method for obtaining a reference waveform at high speed while removing noise therefrom when there is no sample (target measurement object) will be described. However, the apparatus and the method can be similarly applied when there is a sample since the principle is the same.

First Embodiment

As shown in FIG. 1A, in a first embodiment, a terahertz wave generated by a terahertz-wave generator 1 is detected by a terahertz-wave detector 2. A detected signal is amplified by an amplifier 3 and is converted from an analog signal to a digital signal by an A/D converter 4 before being taken into a computer 5. In this embodiment, the terahertz-wave generator 1 and the terahertz-wave detector 2 are respectively configured to generate and detect the terahertz wave by using photoconductors (not shown). Laser light from a laser light source 6 is emitted to the photoconductor within the terahertz-wave generator 1, and is also emitted to the photoconductor within the terahertz-wave detector 2 after being time-delayed by a delay unit 7. The laser light source 6 may be a femtosecond laser or a fiber laser. For example, by scanning a stage set in the delay unit 7 and used for time-delaying, data of the entire terahertz waveform can be obtained. A bias voltage controller 8 is configured to control a voltage applied to the photoconductor within the terahertz-wave generator 1. The photoconductors used in this case are respectively capable of generating and detecting a terahertz wave with a frequency ranging between 0.1 THz and 3.0 THz. A method of generating and detecting a terahertz wave using photoconductors is known as THz-TDS (terahertz time-domain spectroscopy), and a signal obtained by the terahertz-wave detector 2 using a sampling technique corresponds to a time waveform (first time waveform) of a terahertz wave.

The computer 5 has a forming unit 9 therein. The forming unit 9 forms a terahertz waveform (second terahertz waveform (second time waveform)) suited for signal processing and having a high correlation with a mother wavelet. In order to form the second terahertz waveform, it is necessary to measure a terahertz waveform with a good S/N ratio in advance. Therefore, the time waveform of the terahertz wave is obtained by stopping the stage of the delay unit 7 at each point and accumulating signals at the respective points of the stage. Alternatively, the data of the entire waveform may be repeatedly obtained at high speed, and the repeatedly obtained waveforms at the respective points may be added together and averaged out (rapid scan technique). With such control, a terahertz waveform (first terahertz waveform) with a good S/N ratio can be obtained in advance. Subsequently, a wavelet transform is performed on the first terahertz waveform having the good S/N ratio obtained in this manner. As a mother wavelet to be used for the wavelet transform, Coiflet 4, Symlet 10a, or the like having a relatively high correlation with the terahertz waveform is selected.

Figure 2A:
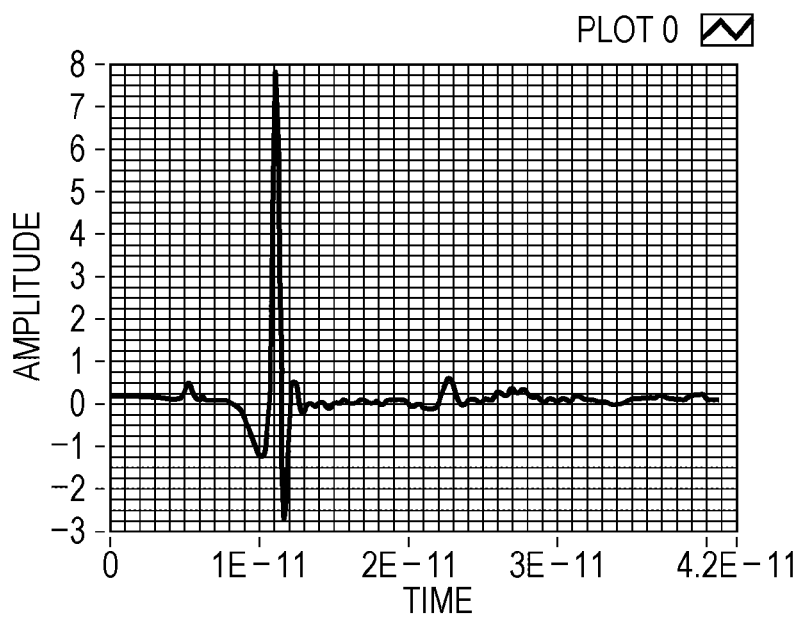
FIG. 2A illustrates a time waveform of a terahertz wave with a good S/N ratio.
Figure 2B:
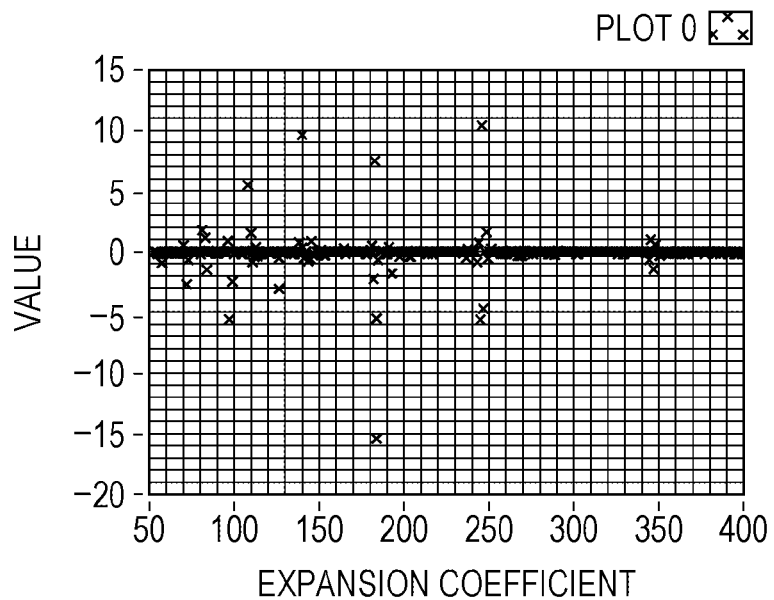
FIG. 2B illustrates wavelet expansion coefficients obtained when a wavelet transform is performed on the time waveform.

FIG. 2A illustrates the time waveform of the terahertz wave with the good S/N ratio obtained in advance by the rapid scan technique. The abscissa indicates time, whereas the ordinate denotes amplitude (i.e., the intensity of the terahertz wave). The number of data points of the terahertz wave is 1024 points. FIG. 2B illustrates a region corresponding to large values, in extracted form, among expansion coefficients obtained when the wavelet transform is performed on the time waveform of the terahertz wave in FIG. 2A. The abscissa denotes the expansion coefficients, whereas the ordinate denotes the value (magnitude) of each expansion coefficient. Although the expansion coefficients are plotted from 50 to 400 in FIG. 2B, the values thereof are not entirely zero. Specifically, an expansion coefficient whose value is plotted close to zero is not exactly zero but has a value close to zero, such as 0.0114275. What can be said here is that, even with a terahertz wave having a good S/N ratio, that is, a terahertz wave from which noise is sufficiently removed, when a wavelet transform is performed on the terahertz wave, the original waveform cannot be expressed unless a significant number of wavelet expansion coefficients are used. In this case, the aforementioned Coiflet 4 is used as the mother wavelet for the wavelet transform.

Figure 3A:
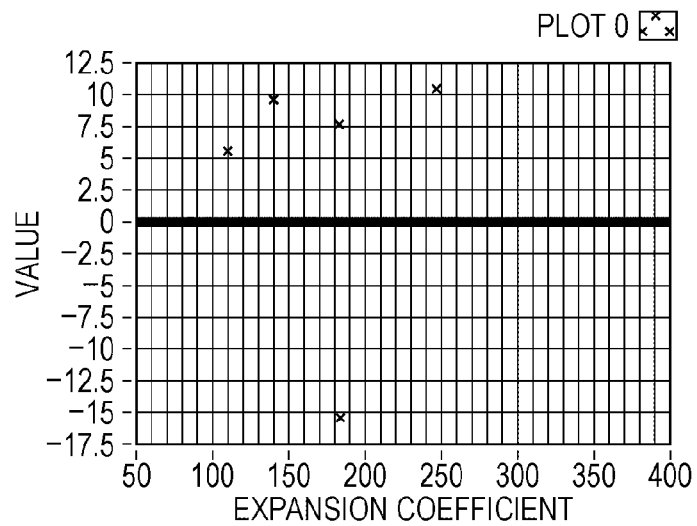
FIG. 3A illustrates the wavelet expansion coefficients after undergoing control.
Figure 3B:
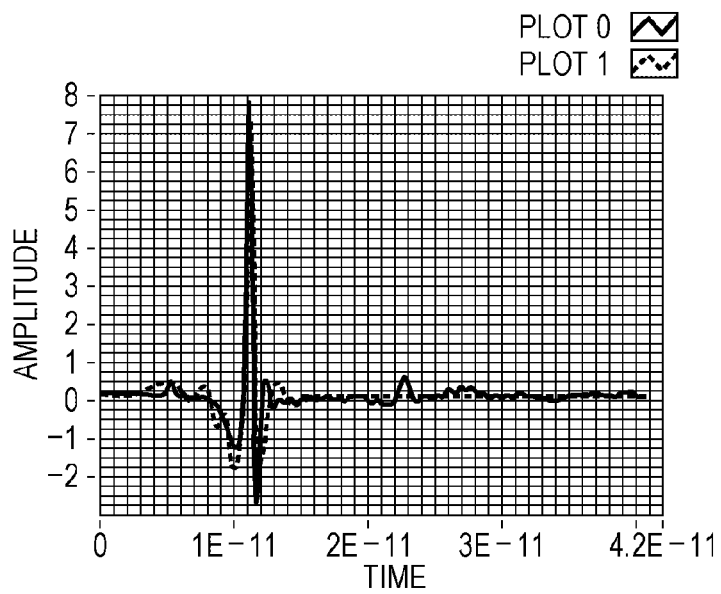
FIG. 3B illustrates a waveform obtained by performing an inverse wavelet transform after controlling the wavelet expansion coefficients.

The following is a conceivable way to express the terahertz waveform with a smaller number of expansion coefficients by controlling the wavelet expansion coefficients. FIG. 3A illustrates a diagram in which the wavelet expansion coefficient values in FIG. 2B that are 5.6 or smaller have been replaced with zero so as to reduce the number of wavelet expansion coefficients to five. If the value of 5.6 is changed to a value greater than 5.6, the number of wavelet expansion coefficients having the value becomes smaller than five. If the value of 5.6 is changed to a value smaller than 5.6, the number of wavelet expansion coefficients having the value becomes greater than five. In this case, the value of 5.6 is selected so that the number of wavelet expansion coefficients is reduced to five. A waveform denoted by a dashed line in FIG. 3B is a waveform obtained by performing an inverse wavelet transform after controlling the wavelet expansion coefficients in this manner. For a comparison, a waveform obtained before controlling the wavelet expansion coefficients is shown with a solid line in FIG. 3B. Before the wavelet expansion coefficients are controlled, the terahertz waveform is expressed using all of the expansion coefficients from 50 to 400, as shown in FIG. 2B. In contrast, after the wavelet expansion coefficients are controlled, the terahertz waveform is expressed using only five wavelet expansion coefficients. Although it is apparent from FIG. 3B that the shape of the terahertz waveform somewhat changes between before and after the wavelet expansion coefficients are controlled, characteristics considered to be important in terahertz imaging, such as the peak position and the relative magnitude of the peak, are maintained.

When controlling the wavelet expansion coefficients in this manner, it is necessary to control the wavelet expansion coefficients so that the characteristics required in the terahertz waveform are maintained. If the characteristics of the terahertz waveform can be maintained, it is desirable that the number of wavelet expansion coefficients be reduced as much as possible. The forming unit 9 within the computer 5 performs an inverse wavelet transform after the wavelet expansion coefficients are controlled in this manner so as to form a second terahertz waveform (second time waveform). The ability to express the terahertz waveform with a smaller number of wavelet expansion coefficients implies that the terahertz waveform is a waveform having a higher correlation with the mother wavelet used in the wavelet transform.

Regarding the selection of the aforementioned threshold value used for controlling the expansion coefficients, optimization may be performed in accordance with, for example, the measurement environment, the sample used, and the selected mother wavelet. For example, since changing the type of mother wavelet causes a change in the distribution of the wavelet expansion coefficients, optimization for selecting a threshold value suited for the distribution may be performed.

If a waveform obtained by controlling the wavelet expansion coefficients and performing an inverse wavelet transform can be measured as a terahertz waveform, this means that the terahertz waveform is expressed with a smaller number of wavelet expansion coefficients. The ability to express the terahertz waveform with a smaller number of wavelet expansion coefficients leads to the following explanation. By setting the values of expansion coefficients other than the wavelet expansion coefficients associated with the terahertz waveform to be determined to zero, most of the noise in the terahertz waveform including system noise and the like can be removed even when the terahertz waveform is measured by scanning the stage at high speed. In light of this, the following operation is performed by using a transforming unit. Specifically, by dividing the waveform obtained after controlling the wavelet expansion coefficients by the waveform obtained before controlling the wavelet expansion coefficients for each delay time, a ratio of waveform values for each delay time can be calculated. Thus, by performing multiplication by the aforementioned ratio for each delay time, that is, for each position of the stage of the delay unit when the stage is scanned, the waveform to be obtained after controlling the wavelet expansion coefficients can be obtained at the time of measuring the terahertz waveform. Specifically, the terahertz waveform can be obtained as a transformed terahertz waveform (transformed time waveform).

Figure 4A:
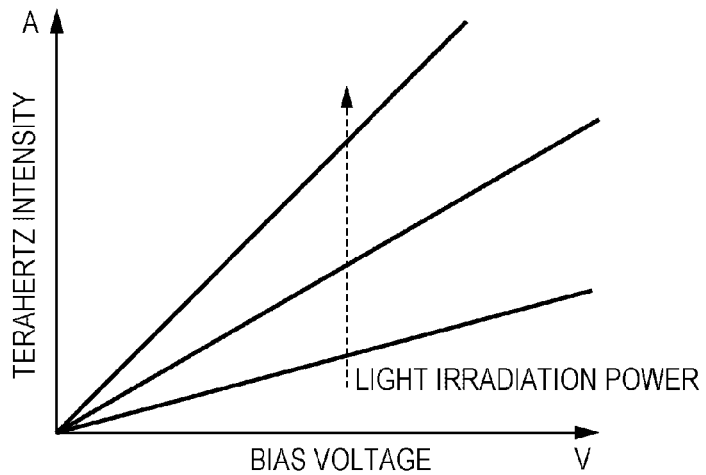
FIG. 4A illustrates the relationship between bias voltage, light irradiation power, and terahertz intensity.

FIG. 4A illustrates the relationship between bias voltage, light irradiation power, and terahertz intensity. Because the terahertz intensity is proportional to the bias voltage if the light irradiation power is constant, the waveform to be obtained after controlling the wavelet expansion coefficients can be obtained at the time of measuring the terahertz waveform by controlling the bias voltage. In this manner, based on the condition in which the light irradiation power is constant, the transforming unit obtains the terahertz waveform by controlling the bias voltage to be applied to the corresponding photoconductor in accordance with each position of the stage of the delay unit by using the bias voltage controller 8 so that the bias voltage corresponds to the aforementioned ratio. Consequently, a transformed terahertz waveform that is the same as that after controlling the wavelet expansion coefficients can be obtained at high speed.

This transformed terahertz waveform obtained at high speed may be used for the target measurement, but may be used for performing the following processing. Specifically, a wavelet transform is performed on the measured waveform (transformed terahertz waveform) obtained in this manner, and an inverse wavelet transform is performed thereon by setting the wavelet expansion coefficients other than the wavelet expansion coefficients determined as being associated with the terahertz waveform to zero when controlling the wavelet expansion coefficients. In this manner, a waveform with a greater amount of noise removed therefrom than in the related art can be obtained.

Figure 4B:
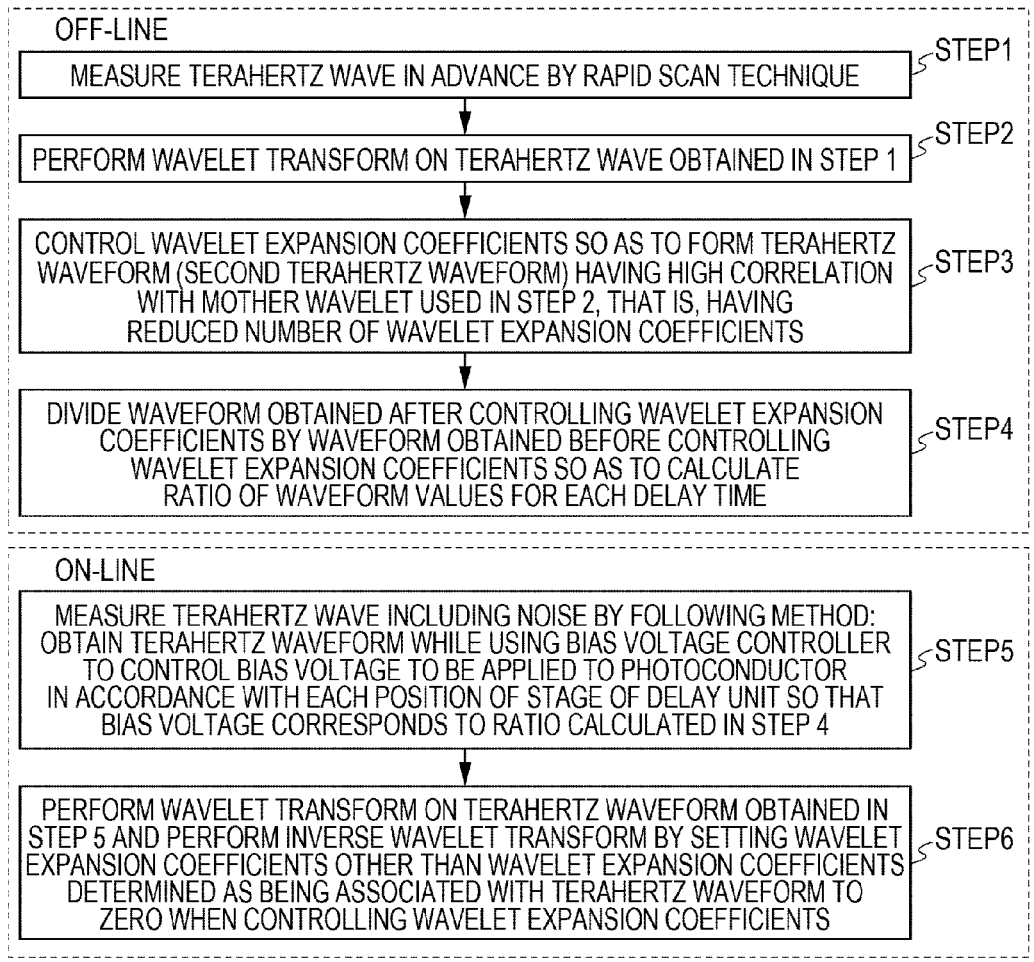
FIG. 4B is a flow chart of a first embodiment of the present invention.

FIG. 4B is a flow chart of the first embodiment, illustrating the aforementioned procedure. The following is a procedure performed off-line. In step 1, a terahertz waveform is measured in advance by, for example, the rapid scan technique. In step 2, a wavelet transform is performed on the terahertz waveform obtained in step 1. In step 3, the wavelet expansion coefficients are controlled so as to form a second terahertz waveform having a high correlation with a mother wavelet used in step 2. In step 4, the waveform obtained after controlling the wavelet expansion coefficients is divided by the waveform obtained before controlling the wavelet expansion coefficients, whereby a ratio of waveform values for each delay time is calculated.

On the other hand, the following steps are executed on-line. In step 5, a terahertz waveform is obtained by using the bias voltage controller 8 to control the bias voltage to be applied to the corresponding photoconductor in accordance with each position of the stage of the delay unit so that the bias voltage corresponds to the ratio calculated in step 4. Consequently, a terahertz waveform containing a certain amount of noise is measured. In step 6, a wavelet transform is performed on the transformed terahertz waveform obtained in step 5, and an inverse wavelet transform is performed thereon by setting the wavelet expansion coefficients other than the wavelet expansion coefficients determined as being associated with the terahertz waveform to zero when controlling the wavelet expansion coefficients.

Second Embodiment

Figure 1B:
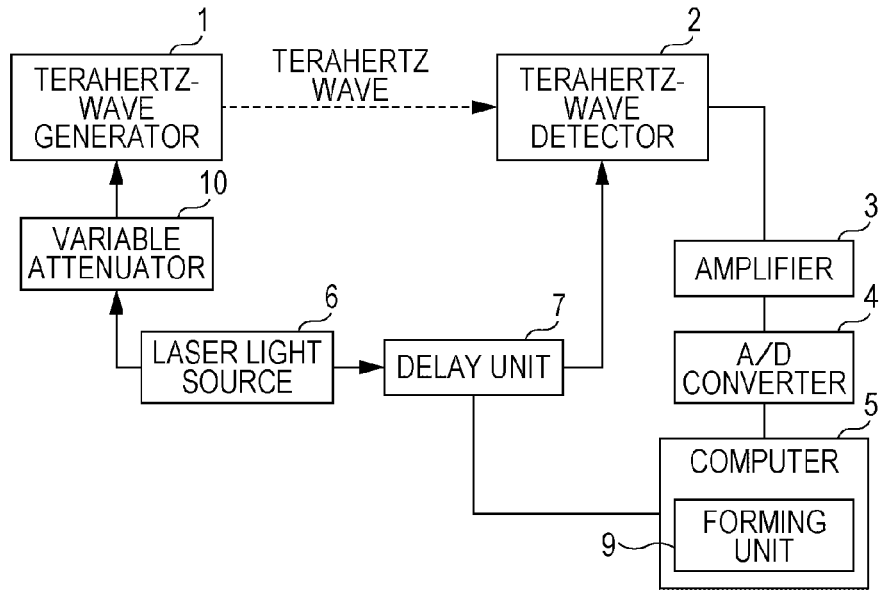
FIG. 1B is a configuration diagram of another embodiment of the present invention.

A second embodiment will now be described with reference to FIG. 1B. The second embodiment differs from the first embodiment in that a variable attenuator 10 is additionally provided between the terahertz-wave generator 1 and the laser light source 6, and that the bias voltage controller 8 is removed. Furthermore, the second embodiment differs from the first embodiment in how the multiplication by the ratio of waveform values calculated from the waveforms obtained before and after controlling the wavelet expansion coefficients is performed for each delay time when measuring the terahertz waveform (transformed terahertz waveform). In the first embodiment, the bias voltage controller 8 is used to control the bias voltage to be applied to the corresponding photoconductor when performing the multiplication by the aforementioned ratio, whereas, in the second embodiment, this bias voltage is fixed to a certain value. Therefore, the bias voltage controller 8 is not necessary.

When the bias voltage is fixed to a certain value, the generated terahertz wave and the light irradiation power to be applied to the photoconductor in the terahertz-wave generator 1 have a proportional relationship (see FIG. 4A). Therefore, in the second embodiment, an attenuation rate of the variable attenuator 10, such as an attenuator, is varied for each delay time so as to control the light irradiation power to be applied to the photoconductor within the terahertz-wave generator 1. In this manner, the multiplication by the aforementioned ratio is performed. With regard to other points, the second embodiment is the same as the first embodiment.

Third Embodiment

Figure 5A:
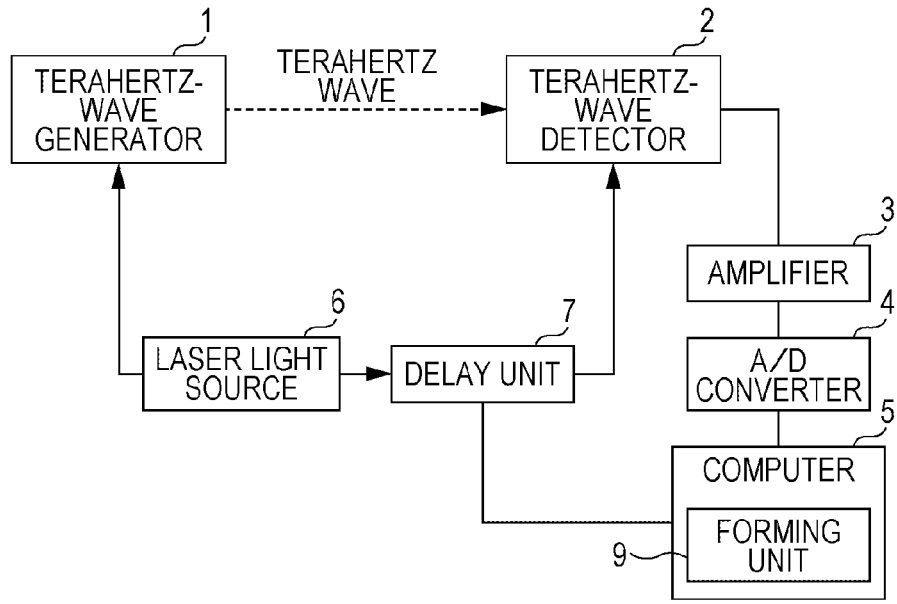
FIG. 5A is a configuration example of a third embodiment of the present invention.

A third embodiment will now be described with reference to FIG. 5A. The third embodiment has a configuration obtained by removing the bias voltage controller 8 from the configuration of the first embodiment. The third embodiment similarly differs from the first embodiment in how the multiplication by the ratio of waveform values calculated from the waveforms obtained before and after controlling the wavelet expansion coefficients is performed for each delay time when measuring the terahertz waveform (transformed terahertz waveform). As in the second embodiment, the bias voltage is fixed to a certain value in the third embodiment. Therefore, the bias voltage controller 8 is not necessary, and the amplification factor of the amplifier 3 for amplifying the signal from the terahertz-wave detector 2 is made variable instead. Specifically, a terahertz waveform (transformed terahertz waveform) is obtained while varying the amplification factor of the amplifier 3, which is fixed in the above embodiments, for each delay time so that the amplification factor corresponds to the aforementioned ratio. With regard to other points, the third embodiment is the same as the first embodiment.

Fourth Embodiment

A fourth embodiment will now be described. A configuration diagram of the fourth embodiment is the same as that of the third embodiment. The fourth embodiment differs from the third embodiment in how the multiplication by the aforementioned ratio is performed for each delay time when measuring the terahertz waveform. Although the amplification factor of the amplifier 3 is varied when performing the multiplication by the aforementioned ratio in the third embodiment, this amplification factor is fixed in the fourth embodiment. Instead, an arithmetic device in the forming unit 9 within the computer 5 performs arithmetic processing for performing the multiplication by the aforementioned ratio for each delay time after the computer 5 loads data of the terahertz waveform as a digital signal. With regard to other points, the fourth embodiment is the same as the third embodiment.

Fifth Embodiment

A fifth embodiment relating to a tomographic imaging system that uses an electromagnetic-wave measuring apparatus will now be described. Generally, when a terahertz waveform is measured, a time waveform of the terahertz wave includes not only large pulses related to imaging, but also small pulses caused by the effect of water vapor in the atmosphere (see FIG. 2A). Therefore, after the terahertz waveform undergoes a wavelet transform and is taken apart into wavelet expansion coefficients, an inverse wavelet transform is performed by setting the values of wavelet expansion coefficients that correspond to the small pulses to zero (i.e., by controlling the expansion coefficients). For example, by performing a wavelet transform by removing data other than the small pulses (i.e., setting the data to zero) in the actually measured data, the positions of the wavelet expansion coefficients that correspond to the small pulses can be ascertained. Thus, an inverse wavelet transform is performed by setting the values of these expansion coefficients to zero.

In this manner, a terahertz waveform suited for imaging can be formed. This terahertz waveform serves as a second terahertz waveform. Subsequently, when actually measuring the terahertz waveform, the value of data obtained for each delay time is varied, thereby obtaining a transformed terahertz waveform. By performing mapping by setting information (such as refractive index) obtained from the transformed terahertz waveform in correspondence with the position of a measurement target obtained from the waveform so as to obtain a tomographic image, an image with an improved S/N ratio can be obtained.

Sixth Embodiment

Figure 5B:
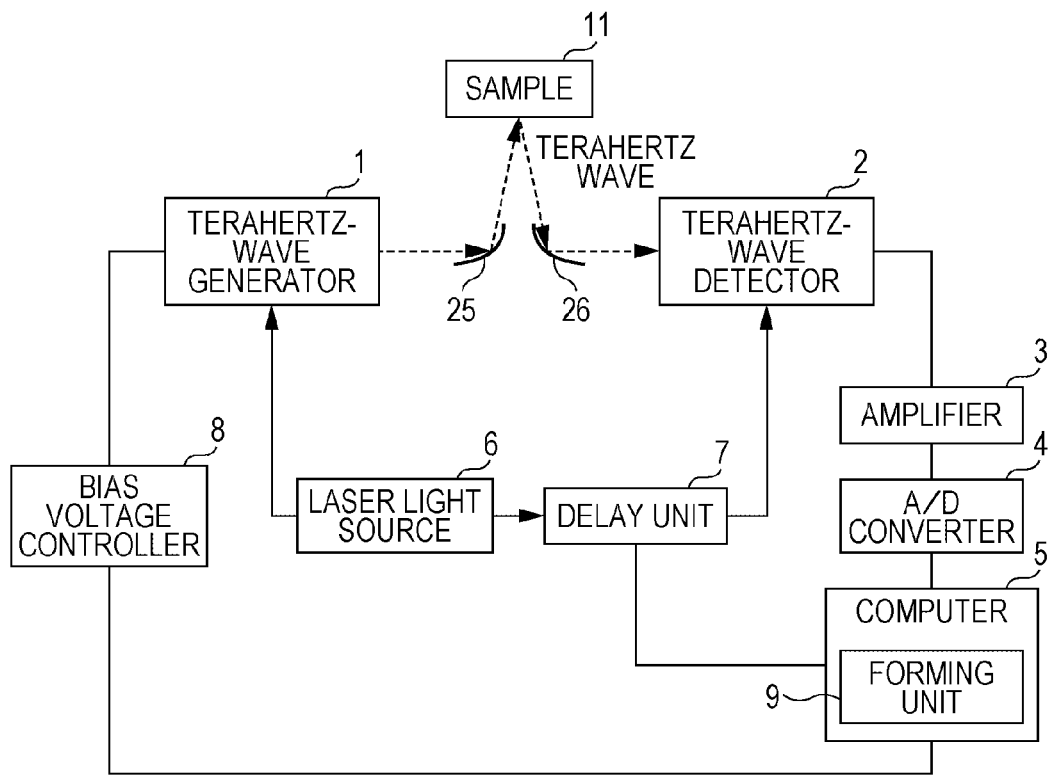
FIG. 5B is a configuration example of a sixth embodiment of the present invention.

A sixth embodiment, which is another embodiment of a tomographic imaging system that uses an electromagnetic-wave measuring apparatus, will now be described. FIG. 5B is a configuration diagram of the sixth embodiment. The basic configuration is the same as that in FIG. 1A, but the sixth embodiment differs therefrom in that the terahertz wave from the terahertz-wave generator 1 is irradiated onto a sample 11 by using a parabolic mirror 25, and a reflection wave from the sample 11 is detected by the terahertz-wave detector 2 via a parabolic mirror 26.

Figure 3C:
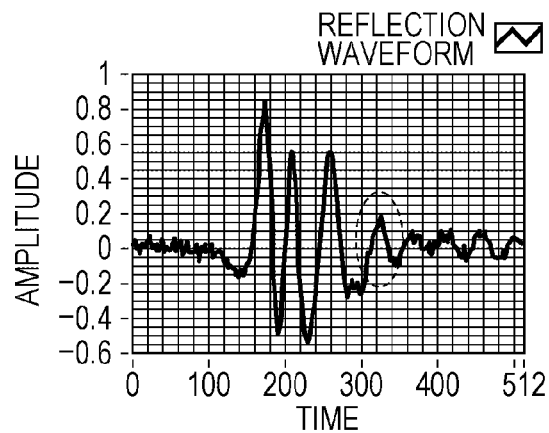
FIG. 3C illustrates a reflection waveform obtained when three layered sheets of paper are used.

FIG. 3C illustrates a reflection waveform obtained when three layered sheets of paper are used as a sample. It is apparent from FIG. 3C that excess multiple reflections are measured in addition to pulses reflected at each of the three sheets of paper (see a section surrounded by a dotted line in FIG. 3C). In the tomographic imaging system using the terahertz-wave measuring apparatus according to the present invention, the excess multiple reflections can be removed. When performing imaging by irradiating a terahertz wave onto a layered sample, such as multiple layered sheets of paper, and measuring a reflection wave therefrom, the obtained image is sometimes affected by multiple reflections, making it difficult to obtain a desired image. In view of this, as in the fifth embodiment, a wavelet transform is performed on a time waveform of the terahertz wave of the measured reflection wave, and an inverse wavelet transform is performed thereon by setting the wavelet expansion coefficients associated with an unnecessary reflection wave to zero (i.e., by controlling the expansion coefficients). In this manner, a terahertz waveform suited for imaging can be formed, and this terahertz waveform serves as a second terahertz waveform. Subsequently, when actually measuring the terahertz waveform, the value of data obtained for each delay time is varied, as in the fifth embodiment, thereby obtaining a transformed terahertz waveform. By obtaining a tomographic image in this manner, an image with unnecessary multiple reflections removed therefrom can be obtained.

Before performing the wavelet transform on the time waveform of the terahertz wave of the measured reflection wave and performing the inverse wavelet transform by setting the expansion coefficients associated with the unnecessary reflection wave to zero, a deconvolution process may be performed on the time waveform of the terahertz wave of the measured reflection wave. For example, in place of paper serving as a sample, a metallic member that reflects the terahertz wave well may be placed at the sample position, and the wavelet transform may be performed on the terahertz waveform obtained after performing the deconvolution process using the time waveform of the terahertz wave at that time as a reference (reference waveform). Specifically, by using an electromagnetic wave corresponding to when the first electromagnetic waveform is entirely reflected at the sample position or by using an electromagnetic wave corresponding to when there is no sample as a reference, an electromagnetic wave when there is a sample may be made to have the time waveform obtained after performing the deconvolution process. By performing the deconvolution process, distortion in the waveform deriving from the system can be removed.

Seventh Embodiment

A seventh embodiment relating to a material determination apparatus that performs determination of a material by using an electromagnetic-wave measuring apparatus will now be described. Determination of whether or not a sample is a material having a characteristic spectrum will be discussed below. A time waveform of a terahertz wave of a sample having a characteristic spectrum is measured in advance. Then, when measuring a terahertz wave of a sample not certain as to whether or not it has a characteristic spectrum, each obtained data item is divided by each terahertz wave value of the sample having the characteristic spectrum measured in advance for each delay time.

Figure 6A:
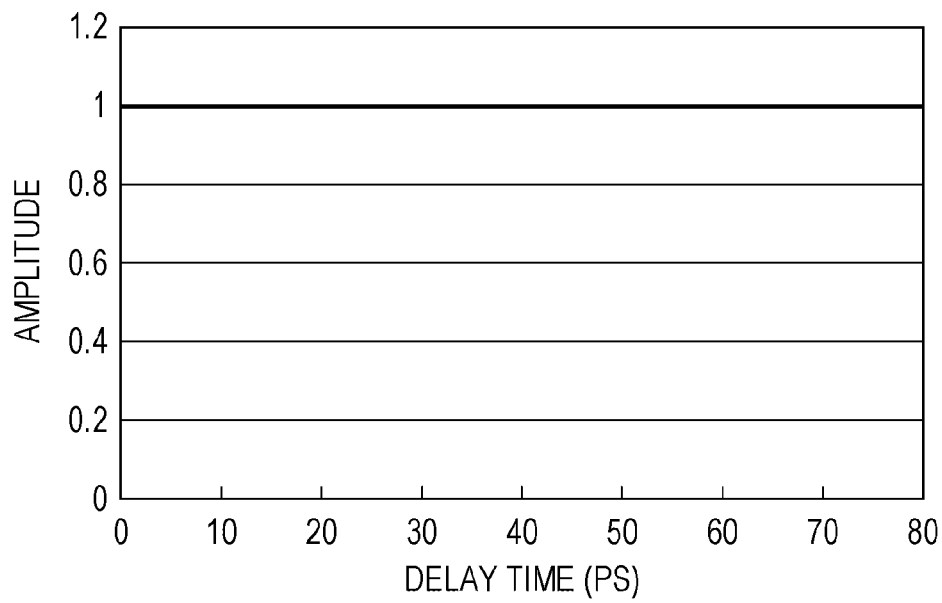
FIG. 6A illustrates a measured waveform corresponding to when a sample has a characteristic spectrum in a seventh embodiment of the present invention.
Figure 6B:
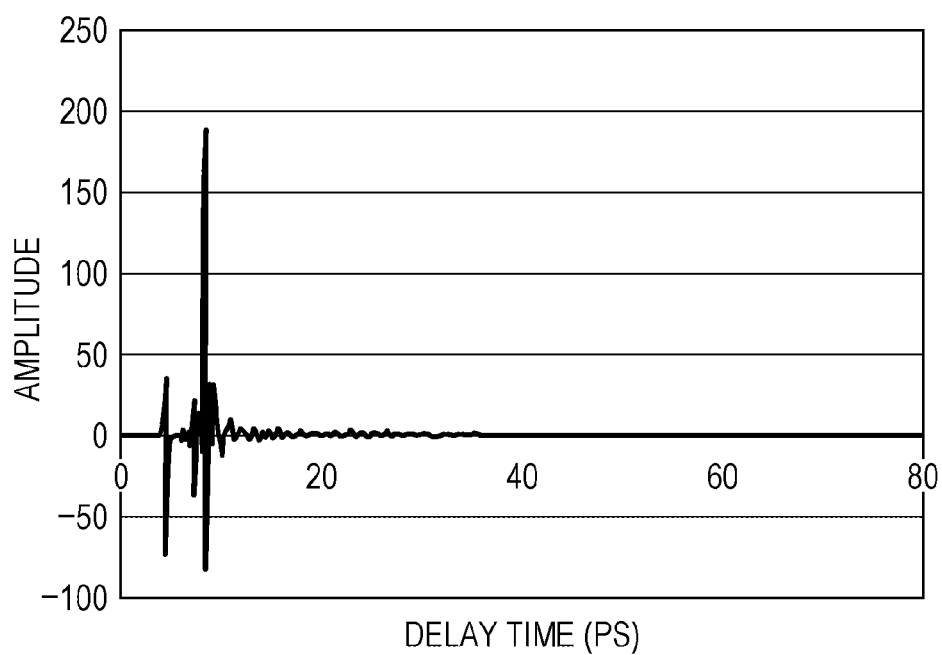
FIG. 6B illustrates a measured waveform corresponding to when a sample does not have a characteristic spectrum in the seventh embodiment of the present invention.

If the sample is a material having a characteristic spectrum, the obtained waveform is flat, as in FIG. 6A. If the sample is not a material having a characteristic spectrum, the obtained waveform is not flat, as in FIG. 6B. In this case, it can be considered that a second terahertz wave has a flat waveform with a value of 1. In this manner, each obtained data item is divided by each terahertz wave value of the sample having the characteristic spectrum measured in advance, and the resultant waveform is determined whether or not it is flat. If the resultant waveform is flat, the sample can be determined as being a sample having a characteristic spectrum, whereas if the resultant waveform is not flat, the sample can be determined as being a sample not having a characteristic spectrum. Since each obtained data item cannot be divided by an exact zero, if each terahertz value of the sample having the characteristic spectrum is an extremely small value, such as zero or close to zero, it is necessary to perform the division by replacing the value with, for example, 0.1 or 0.01, where appropriate. Although a value close to zero, such as 0.01, is generally used, dividing the value by 0.01 is equivalent to multiplying the value by 100. This is fine if it does not cause a problem, but since the y-axis scale is correspondingly increased by 100 times, the value may alternatively be divided by 0.1 (multiplied by 10) depending on the circumstances. This simply implies that the y-axis scale changes.

Other Embodiments

The present invention can also be achieved by executing the following processing. Specifically, the processing involves loading software (program) that has the functions described in the above embodiments into a system or an apparatus via a network or various kinds of storage media and making a computer (or a CPU or an MPU) of the system or the apparatus read and execute the program. The storage medium may be of any type that is capable of storing the program to be executed by the computer. The storage medium is a computer-readable storage medium that stores the program for making the computer execute the above-described electromagnetic-wave measuring method.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-002481, filed Jan. 8, 2010, which is hereby incorporated by reference herein in its entirety.

The invention claimed is:

1. A terahertz electromagnetic wave measuring apparatus for measuring a measured terahertz electromagnetic wave, comprising:
    a generating unit configured to generate a reference terahertz electromagnetic wave;
    a waveform obtaining unit configured to obtain a first reference time waveform from the reference terahertz electromagnetic wave received in dependence of plural delay times;
    a forming unit configured to perform a wavelet transform on the first reference time waveform to obtain reference expansion coefficients based on a mother wavelet, wherein the reference expansion coefficients include at least one expansion coefficient whose absolute value is greater than a threshold, and to perform an inverse wavelet transform by using only the at least one expansion coefficient so as to form a second reference time waveform in dependence of the delay times,
    wherein
    the forming unit is configured to calculate respective ratios of the second reference time waveform and the first reference time waveform for each of the delay times;
    the generating unit is configured to generate the measured terahertz electromagnetic wave, wherein, for each of the plural delay times, the measured terahertz electromagnetic wave corresponds to the reference terahertz electromagnetic wave multiplied by the respective ratio;
    the waveform obtaining unit is configured to obtain a first measured time waveform of the measured electromagnetic wave in dependence of the delay times;
    the forming unit is configured to perform the wavelet transform on the first measured time waveform to obtain measured expansion coefficients based on the mother wavelet, to perform an inverse wavelet transform by using only those of the measured expansion coefficients corresponding to the at least one expansion coefficient so as to form a second measured time waveform in dependence of the delay times.

2. The electromagnetic-wave measuring apparatus according to claim 1, wherein the generating unit comprises a photoconductor, and
    a bias voltage controller configured to control a bias voltage to be applied to the photoconductor or a variable attenuator configured to adjust an intensity of light to be irradiated onto the photoconductor.

3. The electromagnetic-wave measuring apparatus according to claim 1, wherein the transforming unit is an arithmetic unit provided for a computer.

4. A terahertz electromagnetic wave measuring apparatus for measuring a terahertz electromagnetic wave, comprising
    a waveform obtaining unit configured to obtain a first reference time waveform of the terahertz electromagnetic wave in dependence of delay times;
    a forming unit configured to perform a wavelet transform on the first reference time waveform to obtain reference expansion coefficients based on a mother wavelet, wherein the reference expansion coefficients and include at least one expansion coefficient whose absolute value is greater than a threshold, and to perform an inverse wavelet transform by using only the at least one expansion coefficient so as to form a second reference time waveform in dependence of the delay times, wherein the forming unit is configured to calculate respective ratios of the second reference time waveform and the first reference time waveform for each of the delay times;

a transforming unit adapted to obtain a first measured time waveform in dependence of the delay times, wherein, for each delay time, the first measured time waveform corresponds to the first reference time waveform multiplied by the respective ratio;

the forming unit is configured to perform the wavelet transform on the first measured time waveform to obtain measured expansion coefficients based on the mother wavelet, to perform an inverse wavelet transform by using only those of the measured expansion coefficients corresponding to the at least one expansion coefficient so as to form a second measured time waveform in dependence of the delay times.

5. The electromagnetic-wave measuring apparatus according to claim 4, wherein the waveform obtaining unit includes a generator configured to generate the electromagnetic wave, a detector configured to detect the electromagnetic wave, and a delay unit configured to adjust the delay times between a point at which the electromagnetic wave is generated and a point at which the electromagnetic wave is detected, and wherein the first time waveform of the electromagnetic wave is obtained by varying the delay times using the delay unit.

6. The electromagnetic-wave measuring apparatus according to claim 5, wherein the generator is a photoconductor, and wherein the transforming unit is a variable amplifier configured to variably amplify a signal from the detector.

7. The electromagnetic-wave measuring apparatus according to claim 4, wherein the transforming unit is an arithmetic unit provided for a computer.

8. A terahertz electromagnetic wave measuring method for measuring a measured terahertz electromagnetic wave, comprising:

generating a reference terahertz electromagnetic wave;

obtaining a first reference time waveform from the reference terahertz electromagnetic wave received in dependence of plural delay times;

performing a wavelet transform on the first reference time waveform to obtain reference expansion coefficients based on a mother wavelet, wherein the reference expansion coefficients include at least one expansion coefficient whose absolute value is greater than a threshold, and performing an inverse wavelet transform by using only the at least one expansion coefficient so as to form a second reference time waveform in dependence of the delay times;

calculating respective ratios of the second reference time waveform and the first reference time waveform for each of the delay times;

generating the measured terahertz electromagnetic wave, wherein, for each of the delay times, the measured terahertz electromagnetic wave corresponds to the reference terahertz electromagnetic wave multiplied by the respective ratio;

obtaining a first measured time waveform of the measured electromagnetic wave in dependence of the delay times;

performing the wavelet transform on the first measured time waveform to obtain measured expansion coefficients based on the mother wavelet, performing an inverse wavelet transform by using only those of the measured expansion coefficients corresponding to the at least one expansion coefficient so as to form a second measured time waveform in dependence of the delay times.

9. A non-transitory computer-readable storage medium configured to store a program for making a computer execute the electromagnetic-wave measuring method according to claim 8.

10. A terahertz electromagnetic wave measuring method for measuring a terahertz electromagnetic wave, comprising obtaining a first reference time waveform of the terahertz electromagnetic wave in dependence of delay times;

performing a wavelet transform on the first reference time waveform to obtain reference expansion coefficients based on a mother wavelet, wherein the reference expansion coefficients include at least one expansion coefficient whose absolute value is greater than a threshold, and performing an inverse wavelet transform by using only the at least one expansion coefficient so as to form a second reference time waveform in dependence of the delay times;

calculating respective ratios of the second reference time waveform and the first reference time waveform for each of the delay times;

obtaining a first measured time waveform in dependence of the delay times, wherein, for each delay time, the first measured time waveform corresponds to the first reference time waveform multiplied by the respective ratio;

performing the wavelet transform on the first measured time waveform to obtain measured expansion coefficients based on the mother wavelet, performing an inverse wavelet transform by using only those of the measured expansion coefficients corresponding to the at least one expansion coefficient so as to form a second measured time waveform in dependence of the delay times.

11. A non-transitory computer-readable storage medium configured to store a program for making a computer execute the electromagnetic-wave measuring method according to claim 10.

* * * * *